(12) United States Patent
Zumbrum

(10) Patent No.: US 11,103,871 B2
(45) Date of Patent: Aug. 31, 2021

(54) SUBSTANTIALLY ASEPTIC ASSEMBLY FOR PROCESSING FLUIDS

(71) Applicant: Sartorius Stedim North America Inc., Bohemia, NY (US)

(72) Inventor: Michael A. Zumbrum, New Oxford, PA (US)

(73) Assignee: Sartorius Stedim North America Inc., Bohemia, NY (US)

( * ) Notice: Subject to any disclaimer, the term of this patent is extended or adjusted under 35 U.S.C. 154(b) by 476 days.

(21) Appl. No.: 15/774,307

(22) PCT Filed: Nov. 11, 2015

(86) PCT No.: PCT/US2015/060159
§ 371 (c)(1),
(2) Date: May 8, 2018

(87) PCT Pub. No.: WO2017/082895
PCT Pub. Date: May 18, 2017

(65) Prior Publication Data
US 2020/0254461 A1  Aug. 13, 2020

(51) Int. Cl.
*B01L 3/00* (2006.01)
*B01L 3/08* (2006.01)
(Continued)

(52) U.S. Cl.
CPC ............. *B01L 3/563* (2013.01); *B01L 3/08* (2013.01); *C12M 23/08* (2013.01); *C12M 23/38* (2013.01);
(Continued)

(58) Field of Classification Search
None
See application file for complete search history.

(56) References Cited

U.S. PATENT DOCUMENTS 2,186,908 A * 1/1940 Page .................... B65D 51/002
   215/248
3,607,659 A * 9/1971 Bloomer ................ C12M 23/08
   435/302.1
(Continued)

FOREIGN PATENT DOCUMENTS

DE   102014004851   10/2015
EP   1591517        11/2005
(Continued)

OTHER PUBLICATIONS

Sanders, Aseptic Laboratory Techniques: Volume Transfers with Serological Pipettes and Micropipettors, 2012, J. Vis. Exp. (63), pp. 1-12 (Year: 2012).*
(Continued)

*Primary Examiner* — Holly Kipouros
(74) *Attorney, Agent, or Firm* — Womble Bond Dickinson (US) LLP

(57) ABSTRACT

Vessel closure assemblies are provided. The vessel closure assemblies may be engaged with vessels. The vessel closure assemblies may each include a vessel closure, inserts such as anchors and fluid conduits extending through the vessel closure, and a respiratory assembly. The respiratory assembly may include a housing and one or more gas permeable membranes. The gas permeable membranes may be oriented substantially perpendicular to a top wall of the vessel closure through which the inserts extend.

19 Claims, 4 Drawing Sheets

(51) Int. Cl.
  *C12M 1/24* (2006.01)
  *C12M 1/00* (2006.01)
  *C12M 1/12* (2006.01)
(52) U.S. Cl.
  CPC ............ *C12M 29/04* (2013.01); *C12M 37/02* (2013.01); *B01L 2200/0689* (2013.01); *B01L 2300/042* (2013.01); *B01L 2300/048* (2013.01)

(56) References Cited

U.S. PATENT DOCUMENTS

| | | | | |
|---|---|---|---|---|
| 5,267,791 | A * | 12/1993 | Christian | ............ B01F 13/0827 215/309 |
| 5,358,872 | A | 10/1994 | Mussi et al. | |
| 6,095,356 | A | 8/2000 | Rits | |
| 2009/0176301 | A1* | 7/2009 | Oldenburg | ............ C12M 27/02 435/297.1 |
| 2012/0125125 | A1* | 5/2012 | Li | ............ A61B 10/0038 73/863 |
| 2012/0125936 | A1* | 5/2012 | Byers | ............ C12M 23/38 220/371 |
| 2013/0189772 | A1* | 7/2013 | Shaikh | ............ B01L 3/50853 435/297.1 |
| 2013/0295660 | A1* | 11/2013 | Fey | ............ C12M 23/24 435/297.1 |
| 2014/0190570 | A1 | 7/2014 | Zumbrum | |
| 2016/0001285 | A1* | 1/2016 | Kreusch | ............ C12M 23/58 422/548 |

FOREIGN PATENT DOCUMENTS

| | | |
|---|---|---|
| JP | 2001-031126 A | 2/2001 |
| JP | 2003125753 | 5/2003 |
| WO | WO96/30274 A1 | 10/1996 |
| WO | WO-2005105977 A1 * | 11/2005 ............ C12M 23/08 |

OTHER PUBLICATIONS

Chinese Office Action for App. No. 201580085184.9, dated Apr. 3, 2020, 10 pgs.
India Office Action for App. No. 201817017634, dated Mar. 23, 2020, 6 pgs.
International Search Report and the Written Opinion of the International Searching Authority for PCT/US2015/060159; dated Aug. 11, 2016.
International Preliminary Report on Patentability for PCT/US2015/060159; dated May 24, 2018.
European Exam Report for App. No. 15908440.9, dated Dec. 10, 2020, 5 pgs.
European Office Action for Application No. 15908440.9, dated May 27, 2021, 4 pgs.

* cited by examiner

SUBSTANTIALLY ASEPTIC ASSEMBLY FOR PROCESSING FLUIDS

TECHNICAL FIELD

This disclosure relates generally to a substantially aseptic assembly for processing fluids that includes a vessel closure with a respiratory assembly configured to allow gas to pass therethrough.

BACKGROUND

During certain manufacturing processes, vessels containing various fluids are used. Often it is necessary to transfer fluid into or out of a vessel during the process and do so in a manner that eliminates or substantially eliminates the possibility of leakage or contamination. In particular, the need to transfer fluid in such a manner often arises in the manufacturing and processing of pharmaceuticals, biopharmaceuticals, or other biotechnology applications where processes are conducted in vessels of varying shapes and sizes. The need for fluid transfer into and out of a vessel arises in other applications and industries as well, including but not limited to, the production of food, cosmetics, paint, chemicals, including hazardous chemicals, and the transfer and handling of semiconductor fluids.

Regardless of the industry, during transfers or sampling, the fluid should not leak or be contaminated. Leakage exposes the contents of the vessels to the environment, thereby compromising the substantially sterile conditions in which the fluid was kept and may expose operators to potentially dangerous fluids. In addition, when making such transfers, it is desirable to keep the environment surrounding a vessel free from contamination by the contents of the vessel or a sample taken therefrom. It is often the case that, throughout the manufacturing process, there is a need to maintain fluid communication with the interior of the vessel by way of, for example, tubing extending through a vessel closure from the exterior of the vessel into the interior of the vessel, or from the interior to the exterior. To accomplish a substantially aseptic and leak-free transfer, it is desirable to control the environment through which the fluid flows. For example, the pathway from a vessel to a sample container should be substantially aseptic along the entire pathway. Furthermore, it is desirable that the vessel closure be safe for use, reliable, and of relatively low-cost construction.

It is also desirable to transfer fluid using a vessel closure that is pre-sterilized and disposable. A pre-sterilized, disposable vessel closure avoids the need for an operator to sterilize the vessel closure for use. Further, certain sterilization processes can damage vessel closures and render them useless before their first use.

In some instances it is further desirable to allow for the transfer of gas into or out of the vessel. It may be desirable to allow the transfer to occur through the vessel closure. Thereby, for example, a standardized vessel may be employed with either a vessel closure configured to allow or not allow respiration, depending on the purpose for which the vessel is being employed and the substance(s) contained therein.

Thus, what is needed is a vessel closure that provides for the transfer of gas into and out of the vessel and which includes one or more apertures to allow fluid transfer into or out of a vessel to which the vessel closure is attached.

SUMMARY

Briefly described, in one aspect there is disclosed an assembly for processing fluids. The assembly may include a vessel having an opening. Further, the assembly may include a vessel closure sealingly engaged to the opening of the vessel. The vessel closure may include one or more apertures extending through the vessel closure. Additionally, the assembly may include one or more inserts extending through the one or more apertures. The assembly may further include a respiratory assembly engaged with the vessel closure. The respiratory assembly may include a housing and one or more gas permeable membranes engaged with the housing.

In some embodiments the vessel closure may have a combined flux greater than approximately 250 $cc^3$/min at 0.5 psig. One or more of the inserts may include a fluid conduit. One end of the fluid conduit may terminate at a first terminus approximately inside the vessel closure.

In some embodiments the vessel closure may have a surface facing an interior surface of the vessel when the vessel closure sealingly engages the vessel, and one end of the fluid conduit may terminate at a first terminus approximately flush with the vessel closure surface facing the interior surface of the vessel. One end of the fluid conduit may terminate at a first terminus inside the vessel and the other end of the fluid conduit may terminate at a second terminus outside the vessel closure and outside the vessel. One end of the fluid conduit may terminate at a second terminus outside the vessel and at least partially outside the vessel closure. The second terminus outside the vessel and at least partially outside the vessel closure may further include a fitting selected from the group consisting of an aseptic connector, an air-tight fitting, a plug, and a needleless luer access site.

In some embodiments the one or more inserts comprise one or more anchors through which fluid conduits pass. The fluid conduits may terminate at a first terminus inside the vessel and may terminate at a second terminus outside the vessel. The fluid conduit terminus located outside the vessel may further include an aseptic connector.

In some embodiments the one or more gas permeable membranes may have a surface area equal to or greater than approximately 154 $mm^2$. At least of one of the one or more inserts may include a barbed fitting that may include two attachment points whereby tubing may be engaged to the barbed fitting at a first attachment point and extend into the interior of the vessel and tubing may be engaged to a second attachment point and extend outside of the vessel.

In some embodiments the respiratory assembly may engage the vessel closure via interference fit. The vessel closure may have an upper surface and the one or more gas permeable membranes may extend substantially perpendicular to the upper surface of the vessel closure. The assembly may further include a plurality of gas permeable membranes. The plurality of gas permeable membranes may extend substantially parallel to one another. The vessel closure may have an upper surface and the plurality of gas permeable membranes may extend substantially perpendicular to the upper surface of the vessel closure. The vessel may include an Erlenmeyer flask.

In an additional aspect a substantially aseptic assembly for processing fluids is provided. The assembly may include a vessel having an opening. Further, the assembly may include a vessel closure sealingly attached to the opening of the vessel. The vessel closure may include one or more apertures extending through the vessel closure. Additionally, the assembly may include one or more inserts extending through the one or more apertures. The assembly may further include a respiratory assembly engaged with the vessel closure. The respiratory assembly may include a housing and one or more gas permeable membranes engaged with the housing. The vessel closure may have an upper surface and the one or more gas permeable membranes may extend substantially perpendicular to the upper surface of the vessel closure. In some embodiments one or more of the inserts may include a fluid conduit.

In a further aspect a method of growing cells in suspension in a vessel is provided. The method may include adding media to the vessel. Further, the method may include adding cells to the vessel. The vessel may have an opening. A vessel closure may be sealingly engaged to the opening of the vessel. The vessel closure may include one or more apertures extending through the vessel closure. The vessel closure may additionally include one or more inserts extending through the one or more apertures. A respiratory assembly may be engaged with the vessel closure. The respiratory assembly may include a housing and one or more gas permeable membranes engaged with the housing. The method may additionally include providing conditions for growing the cells.

Thus, vessel closure assemblies and related methods are disclosed that possess distinct attributes and represent distinct improvements over the prior art. These and other aspects, features, and advantages of the vessel closure assemblies of this disclosure will be better understood and appreciated upon review of the detailed description set forth below when taken in conjunction with the accompanying drawing figures, described briefly below. According to common practice, the various features of the drawings may not be drawn to scale. Dimensions and relative sizes of various features and elements in the drawings may be shown enlarged or reduced to illustrate more clearly the embodiments of the present disclosure.

DETAILED DESCRIPTION OF EMBODIMENTS

Certain exemplary embodiments of the present disclosure are described below and illustrated in the accompanying figures. The embodiments described are only for purposes of illustrating the present disclosure and should not be interpreted as limiting the scope of the disclosure, which, of course, is limited only by the claims below. Other embodiments of the disclosure, and certain modifications and improvements of the described embodiments, will occur to those skilled in the art, and all such alternate embodiments, modifications, and improvements are within the scope of the present disclosure.

Figure 1:
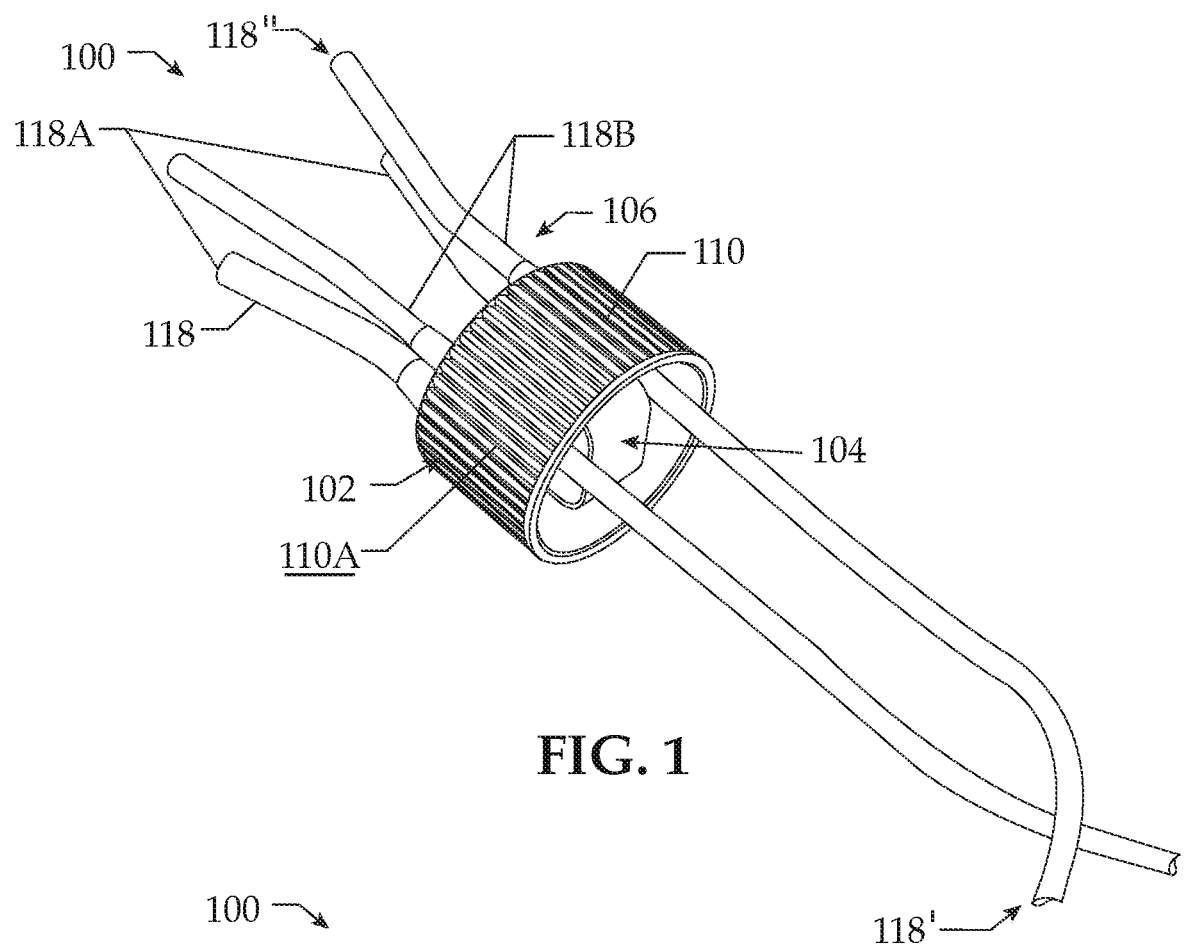
FIG. 1 is a perspective view of a bottom and side of a vessel closure assembly including a vessel closure, a respiratory assembly engaged with the vessel closure, and a plurality of inserts extending through the vessel closure according to an example embodiment of the present disclosure.
Figure 2:
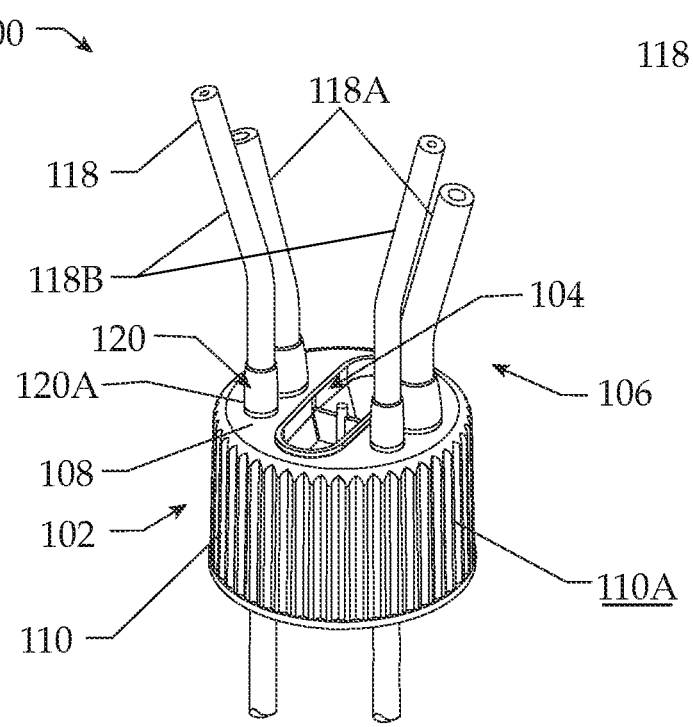
FIG. 2 is a perspective view of a top and the side of the vessel closure assembly of FIG. 1.

Referring now in more detail to the drawing figures, wherein like reference numerals indicate like parts throughout the several views, FIG. 1 illustrates a perspective view of a bottom and side of a vessel closure assembly 100. Further, FIG. 2 illustrates a perspective view of a top and side of the vessel closure assembly 100. As illustrated, the vessel closure assembly 100 may include a vessel closure 102, a respiratory assembly 104, and one or more inserts 106.

In the illustrated embodiment of the vessel closure assembly 100, the vessel closure 102 is a cap. Suitable caps for the vessel closure 102 include those commonly used in the field of pharmaceutical, biopharmaceutical, and biotechnology processing. Such caps include: a 1 L Erlenmeyer flask cap with an inner diameter at the opening end of approximately 43 mm and being approximately 30 mm in height, a 3 L Erlenmeyer flask cap with an inner diameter at the opening end of approximately 70 mm and being approximately 30 mm in height, a 38-430 cap with an outer diameter at the open end of approximately 42 mm and being approximately 29 mm tall, a centrifuge cap having an outer diameter at the open end of approximately 34 mm and being approximately 13 mm tall, a 20-415 cap with an outer diameter at the open end of approximately 24 mm and being approximately 14.6 mm tall, a GL-45 cap having an outer diameter at the open end of approximately 53.7 mm and being approximately 25.5 mm tall, a GL-32 cap having an inner diameter at the opening end of approximately 32 mm and being approximately 26 mm tall, a GL-25 cap having an inside diameter at the open end of approximately 25 mm and being approximately 20 mm in height, bung ports, 53B carboy caps, and 83B carboy caps. The vessel closure 102, however, is not limited to a cap of any particular dimensions. The vessel closure 102 may be made from thermoplastics such as polyolefins, polypropylene, polyethylene, polysulfone, polyester, polycarbonate, and glass filled thermoplastics. The vessel closure 102, however, is not limited to any particular material(s). The vessel closure 102 may also be made from thermosets such as epoxies, pheonolics, and novolacs. The vessel closure 102 may also be a hygienic or sanitary clamp having dimensions disclosed in ASME BPE table DT-5-2 ("Hygienic Clamp Ferrule Standard Dimensions and Tolerances") (2009), which is incorporated by reference herein in its entirety. The vessel closure is not limited to caps or hygienic clamps but may constitute any suitable closure that seals the interior of a vessel from the exterior environment.

Figure 3:
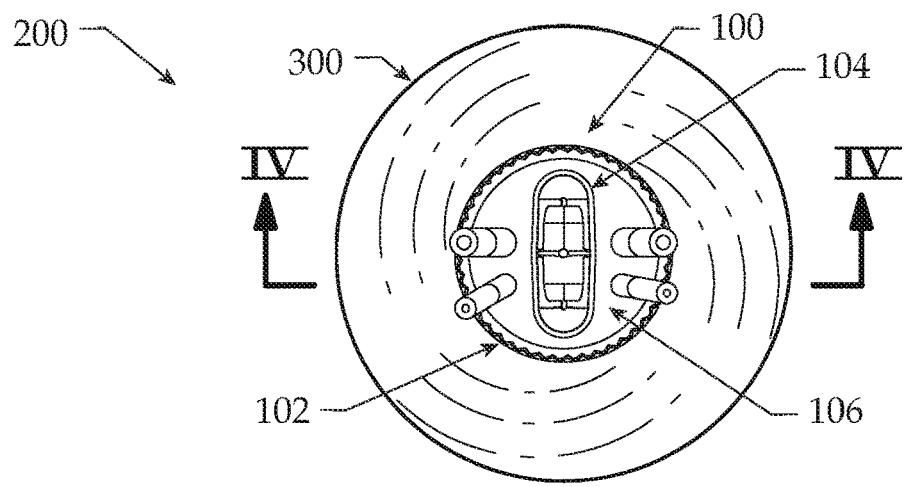
FIG. 3 is a top view of an assembly for processing fluids including the vessel closure assembly of FIG. 1 and a vessel according to an example embodiment of the present disclosure.
Figure 4:
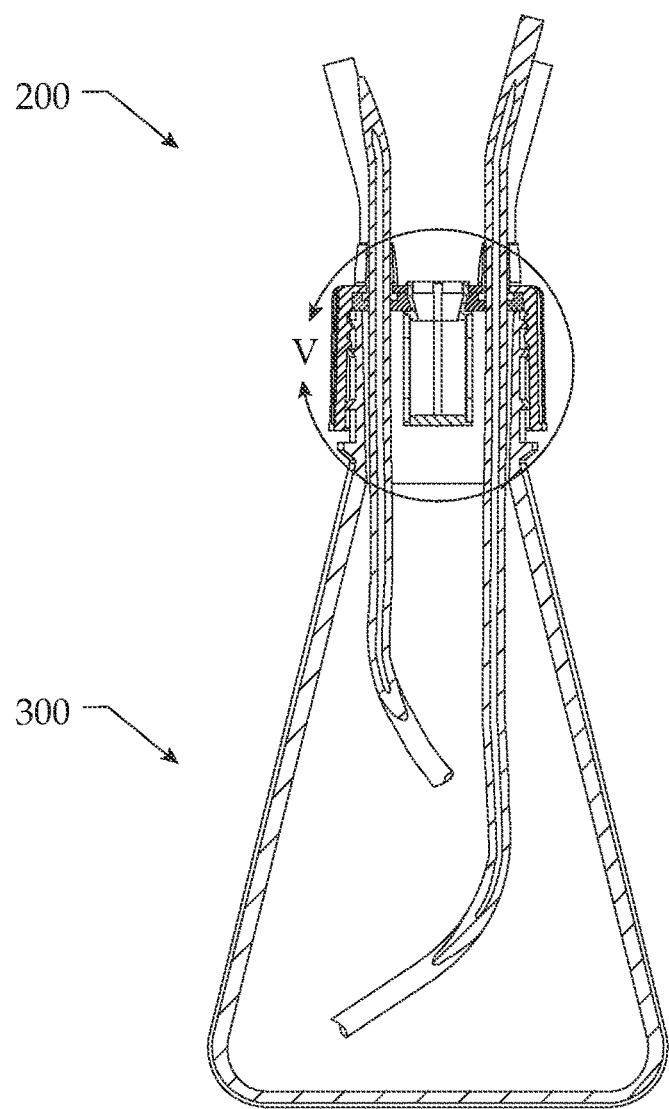
FIG. 4 is a sectional view through the assembly for processing fluids of FIG. 3 along line IV-IV.
Figure 5:
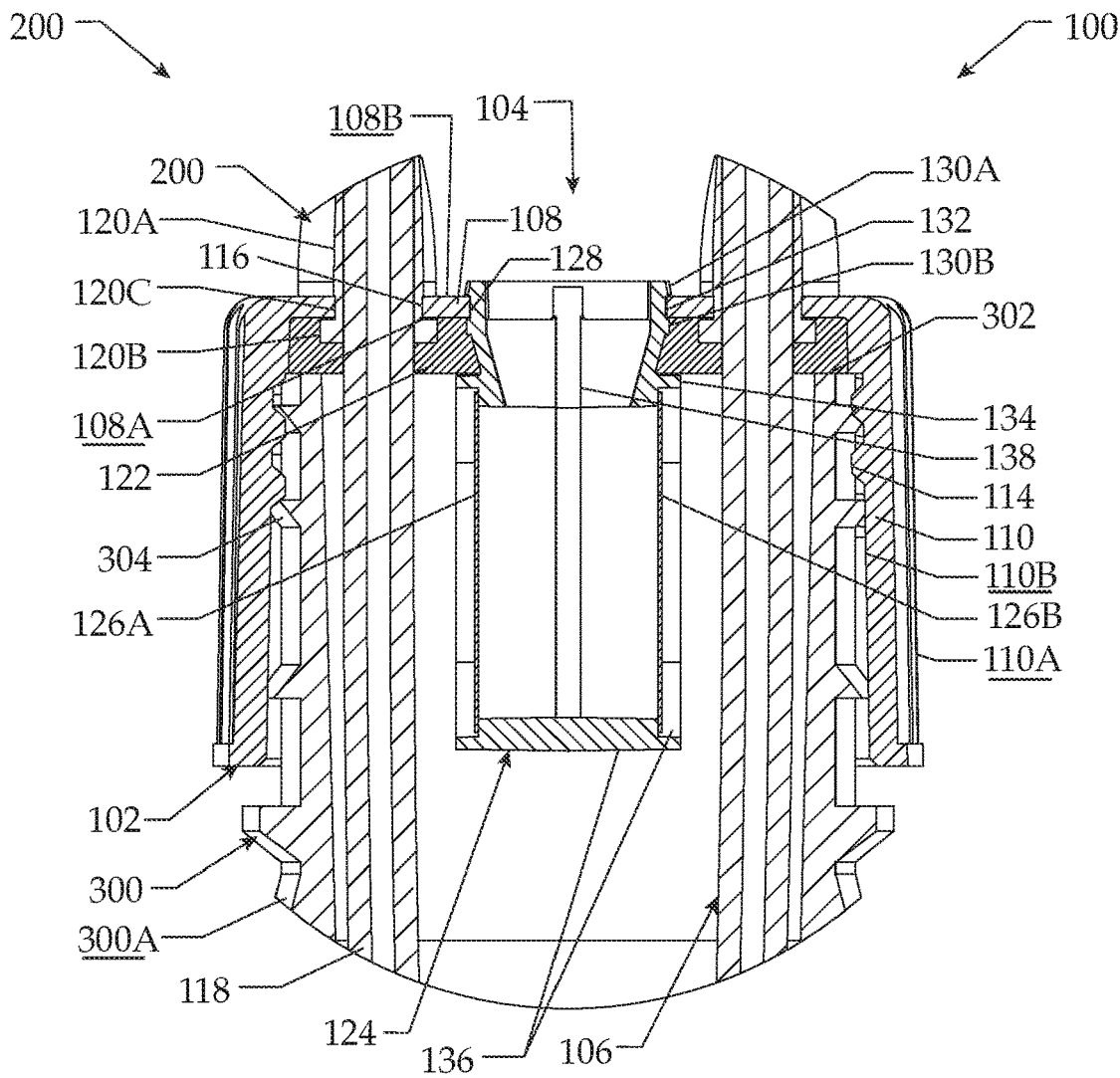
FIG. 5 is an enlarged view of area V from FIG. 4.
Figure 7:
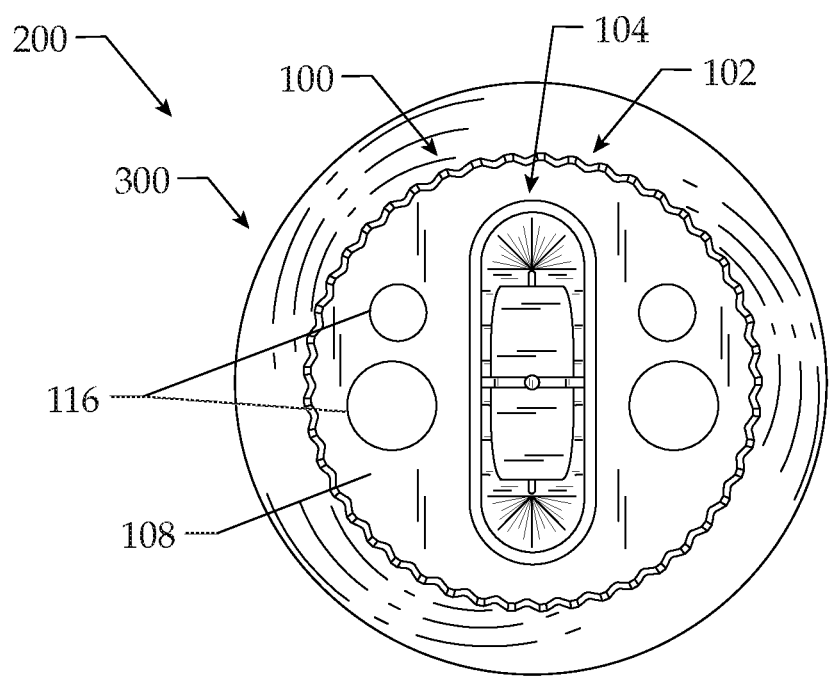
FIG. 7 is a top view of the assembly for processing fluids of FIG. 3 with the inserts removed.

In this regard, FIGS. 3-5 and 7 illustrate an assembly for processing fluids 200, which may include the vessel closure assembly 100 and a vessel 300. In particular, FIG. 3 illustrates a top view of the assembly for processing fluids 200 and FIG. 7 illustrates a corresponding top view of the assembly for processing with the inserts 106 removed, FIG. 4 illustrates a sectional view through the assembly for processing along line IV-IV from FIG. 3, and FIG. 5 illustrates an enlarged view of area V from FIG. 4. As illustrated in FIG. 5, the vessel 300 may include an opening 302, which may be defined at a top thereof. The vessel closure 102 may be sealingly engaged to the opening 302 of the vessel. In some embodiments the assembly for processing fluids 200 may be substantially aseptic to allow for processing of fluids without contamination thereof.

The assembly for processing fluids 200 may include various types of vessels. In the illustrated embodiment the vessel 300 comprises a flask. However, the vessel 300 may additionally comprise, without limitation, bags (e.g., bioreactor bags), bottles, flasks, syringes, containers, beakers, receptacles, tanks, vats, vials, tubes (e.g., centrifuge tubes), and the like that are generally used to contain fluids, slurries, and other similar substances.

Referring to FIGS. 1 and 2, and with regard to the vessel closure assembly 100, in one embodiment the vessel closure 102 may include a top wall 108 and a sidewall 110 connected thereto and extending downwardly therefrom at substantially a right angle. The sidewall 110 may be substantially cylindrical and include an outer surface 110A which may be fluted and include a plurality of groves and ridges, as illustrated in FIGS. 1 and 2. The outer surface 110A may provide improved grip that facilitates twisting the vessel closure 102 during engagement and disengagement with the vessel 300.

In this regard, as illustrated in FIG. 5, the vessel 300 may include a plurality of threads 304. The threads 304 may be defined at an outer surface 300A of the vessel 300 proximate the opening 302. Further, the vessel closure 102 may include a plurality of corresponding threads 114, which may be defined at an inner surface 110B of the sidewall 110. Corresponding threads 114 of the vessel closure 102 may engage the threads 304 of the vessel 300 to bring the vessel closure assembly 300 into engagement with the vessel and seal the opening 302.

Note that although a threaded connection is described above as being employed to engage the vessel closure assembly 100 with the vessel 300, various other connection mechanisms may be employed in other embodiments. By way of example, in other embodiments the connection mechanism may comprise a clamp connection, a welded connection, a bonded connection, or any other mechanical means. Alternatively, the vessel closure may be formed as a singular unit with the vessel. For example, the vessel may be formed in a manner whereby the vessel closure is formed as an integral component of the vessel when the vessel is manufactured. Regardless of whether the vessel closure is a separate component, or formed as an integral part of the vessel, the vessel closure and the vessel form a leak-free connection.

With further regard to the vessel closure assembly 100, as shown in FIG. 7, one or more apertures 116 may extend through the vessel closure 102. In particular, the apertures 116 may extend through the top wall 108 of the vessel closure 102. The apertures 116 may be made using a punch press, a drill, mill, laser, or any combination thereof. In another embodiment, the apertures 116 are molded when the vessel closure is molded.

The one or more inserts 106 may be engaged with and extend through the one or more apertures 116 defined through the vessel closure 102 as illustrated, by way of example, in FIG. 5. Various embodiments of the inserts 106 may be employed. In some embodiments one or more of the inserts 106 may comprise a fluid conduit 118. As illustrated in FIG. 1, each of the fluid conduits 118 may extend between a first terminus 118' and a second terminus 118". The first terminus 118' may be configured to be positioned in direct fluid communication with the vessel 300. In this regard, the first terminus 118' may be positioned at or within an interior of the vessel closure 102 and/or at or within an interior of the vessel 300 when the vessel closure assembly 100 is coupled thereto.

For example, a portion 118A of the fluid conduits 118 terminate at a first terminus (not shown) positioned approximately inside the vessel closure 102. In other words, the first terminus of portion 118A of the fluid conduits 118 may be positioned within an interior of the vessel closure 102, which is defined by the top wall 108 and the sidewall 110 thereof in the illustrated embodiment. Accordingly, as a result of the first terminus being positioned approximately inside the vessel closure 102, the first terminus of the portion 118A of the fluid conduits 118 are not visible in FIG. 1. By way of example, the first terminus of a fluid conduit may extend through the vessel closure 102 and into the interior of a vessel 300. The fluid conduit 118 may extend into the interior of the vessel 300 and terminate at a first terminus (not shown) that extends into the vessel interior a distance that is approximately equal to the depth that the respiratory assembly 104 extends into vessel interior, thereby allowing the fluid conduit 118 to dispense fluid into the vessel and avoid fluid contacting the respiratory assembly 104. In one example, a fluid conduit may extend into the interior of the vessel approximately 25 mm.

By way of further example, the vessel closure 102 may have a surface (e.g., a lower surface 108A of the top wall 108; see, e.g., FIG. 5) facing the interior surface of the vessel 300 once sealingly engaged to the vessel, and one end of the fluid conduit 118A may terminate at a first terminus approximately flush with the vessel closure surface (e.g., the inner surface of the top wall) facing the interior surface of the vessel. The fluid conduits 118A that include a first terminus (not shown) positioned within the interior of the vessel closure 102 may be configured, for example, to direct a gas into or out of the vessel 300 to which the vessel closure 102 is attached or to dispense liquids from a height above the surface of the liquid received therein.

Conversely, all or a portion 118B of the fluid conduits 118 may extend through the apertures 116 and terminate at a first terminus 118' configured to extend inside the vessel 300 to which the vessel closure assembly 100 is coupled. The fluid conduits 118B that include a first terminus 118' positioned within the vessel 300 to which the vessel closure 102 is attached may be configured, for example, to draw liquid from the vessel or direct liquid into the vessel proximate to the bottom thereof with a minimum of turbulence.

Whereas the fluid conduits 118 may terminate at a position within the vessel closure 102 or within the vessel 300, the fluid conduits 118 may terminate at a second terminus, for example terminus 118", outside the vessel. Further, the second terminus 118" of the fluid conduits 118 may terminate at least partially outside the vessel closure 102. The second terminus 118" may in some embodiments include a fitting. Examples of fittings that may be included at the second terminus 118" may be selected from the group consisting of an aseptic connector, an air-tight fitting, a plug, and a needleless luer access site.

It should be understood that the vessel closure assembly 100 is not limited to use with any particular fluids. However, depending on the size and composition of the vessel closure assembly 100 and its constituent fluid conduits 118, the vessel closure assembly 100 may be used with fluids with particulates or having a high viscosity or with fluids having no or very little particulate content or low viscosity.

As illustrated in FIG. 2, the one or more inserts 106 may further comprise anchors 120. The anchors 120 may be configured to secure the fluid conduits 118 to the vessel closure 102. For example, the anchors 120 may include a tapered section 120A, which may be substantially conical, and a flange 120B (see, e.g., FIG. 5). In some embodiments the anchors 120 may further comprise a groove 120C, which may be positioned between the tapered section 120A and the flange 120B.

During assembly, the fluid conduit 118 may be inserted through the anchor 120, or the anchor may be integrally formed with the fluid conduit. Thereby, the fluid conduit 118 may extend or pass through the anchor 120. Further, the fluid conduit 118 and the anchor 120 may be inserted through an aperture 116 defined through the vessel closure 102. In particular, the tapered section 120A of the anchor 120 may be inserted through the aperture 116 such that the groove 120C engages the aperture and the flange 120B contacts the lower surface 108A of the top wall 108 of the vessel closure 102, as illustrated in FIG. 5. Thereby, the anchor 120 may be friction or interference fit into the aperture 116 in the vessel closure 102 by pressing the tapered section 120A into and through the aperture until the flange 120B is secured to the vessel closure 102.

Thus, the anchor 120 may seal against both the vessel closure 102 and the fluid conduit 118 so as to prevent fluid leakage at the apertures 116. However, as illustrated in FIG. 5, in some embodiments the vessel closure assembly 100 may further comprise a cast seal 122. The cast seal 122 may surround, secure, and seal the fluid conduits 118 and/or the anchors 120 to the vessel closure 102. Utilizing a cast seal 122 allows for integration of the fluid conduits 118 from within the vessel closure 102 or within the vessel 300 to a point exterior of the vessel, as described above, thereby providing a continuous fluid pathway without the use of connectors such as barbed or luer connectors.

In one embodiment the cast seal 122 is constructed from a self-leveling, pourable silicone such as room-temperature-vulcanizing ("RTV") silicone. The RTV silicone may be a two-component system (base plus curative) ranging in hardness from relatively soft to a medium hardness, such as from approximately 9 Shore A to approximately 56 Shore A. Suitable RTV silicones include Wacker® Elastocil® RT 622, a pourable, addition-cured two-component silicone rubber that vulcanizes at room temperature (available from Wacker Chemie AG), and Rhodorsil® RTV 1556, a two-component, high strength, addition-cured, room temperature or heat vulcanized silicone rubber compound (available from Blue Star Silicones). Both the Wacker® Elastocil® RT 622 and the Bluestar Silicones Rhodorsil® RTV 1556 have a viscosity of approximately 12,000 cP (mPa·s). The aforementioned silicones and their equivalents offer low viscosity, high tear cut resistance, high temperature and chemical resistance, excellent flexibility, low shrinkage, and the ability to cure into the cast seal 122 at temperatures as low as approximately 24° C. (75° F.). The cast seal 122 may also be constructed from dimethyl silicone or low temperature diphenyl silicone or methyl phenyl silicone. An example of phenyl silicone is Nusil MED 6010. Phenyl silicones are particularly appropriate for cryogenic applications. In another embodiment, the casting agent is a perfluoropolyether liquid. An example perfluoropolyether liquid is Sifel 2167, available from Shin-Etsu Chemical Co., Ltd. of Tokyo, Japan.

In an embodiment, the cast seal 122 is disposed within the interior of the vessel closure 102 defined by the top wall 108 and the side wall 110 so that when the vessel closure is connected to or integrally combined into the vessel 300, the cast seal creates an aseptic seal between the interior of the vessel and the exterior of the vessel, due to contact with the vessel proximate the opening 302, thereby protecting an environment within the vessel and maintaining a closed and hygienic system. The seal formed by the fluid conduits 118 between the interior of the vessel 300 and the exterior environment may be substantially aseptic. As illustrated in FIG. 5, the cast seal 122 surrounds the fluid transfer conduits 118 and the anchors 120, thereby creating a seal. In an embodiment, the seal between the cast seal 122 and the inserts 106 is substantially aseptic.

In one embodiment, the inserts 106 may include fluid conduits 118 comprising silicone tubing. The silicone tubing may be of any length suitable and necessary for the desired process. In an embodiment, at least a portion of the silicone tubing is treated with a primer where the cast seal 122 (e.g., cast silicone) surrounds the silicone tubing. Suitable primers are SS-4155 available from Momentive™ Med-162 available from NuSil Technology, and Rodorsil® V-O6C available from Bluestar Silicones of Lyon, France.

In another embodiment, the cast seal 122 is connected to the vessel closure assembly 100 by way of priming at least a portion of the vessel closure 102 and adhesively attaching the cast seal to the vessel closure. In this embodiment, the cast seal 122 will not pull away from the interior of the vessel closure 102.

The fluid conduit 118 may comprise thermoplastic tubing, thermoset tubing, elastomeric tubing, or any combination thereof. If a thermoset is used, silicones, polyurethanes, fluoroelastomers or perfluoropolyethers are example construction materials for the fluid conduits. If a thermoplastic is used, C-Flex® tubing, block copolymers of styrene-ethylene-butylene-styrene, PureWeld, PVC, polyolefins, or polyethylene are example construction materials. Multiple fluid conduits may be used including combinations of elastomeric, thermoset, and thermoplastic materials in the same vessel closure assembly.

When the inserts 106 include anchors 120, the cast seal 122 need not be constructed of cast silicone but may be made of any casting agent capable of bonding to the anchors or other insert. For example, in applications involving solvents, a casting agent such as perfluoropolyether liquid potting material could be used. Primers can be used to enhance bonding to the insert and/or body.

As noted above, the vessel closure assembly 100 may further comprise a respiratory assembly 104. The respiratory assembly 104 may be configured to allow respiration to/from the vessel 300, or allow for respiration by the contents of the vessel, when the vessel closure assembly 100 is coupled thereto.

As illustrated in FIG. 5, the respiratory assembly 104 may include a housing 124 and one or more gas permeable membranes 126A, 126B engaged with the housing. The respiratory assembly 104 may be engaged with the vessel closure 102. For example, the respiratory assembly 104 may engage the vessel closure 102 via interference fit. In this regard, the vessel closure 102 may include an aperture 128 that extends through the top wall 108 thereof. In some embodiments the aperture 128 may be centrally disposed in the top wall 108. Thereby, the apertures 116 through which the inserts 106 extend may be positioned generally radially outward therefrom. This configuration provides for improved access to the inserts 106 while avoiding obstructing the respiratory assembly 104.

The respiratory assembly 104 may be inserted through the aperture 128 into engagement with the top wall 108 of the vessel closure 102. For example, in the illustrated embodiment in FIG. 6, the housing 124 includes first and second ridges 130A, 130B and a recess 132 positioned therebetween. Thereby, the respiratory assembly 104 may be inserted upwardly through the aperture 128 such that the first ridge 130A engages an upper surface 108B of the top wall 108 of the vessel closure 102, the recess 132 engages the aperture 128, and the second ridge 130B engages the lower surface 108B of the top wall of the vessel closure. Further, the housing 124 may include a flange 134 that may be in contact with the cast seal 122. In this regard, the cast seal 122 may be formed after the respiratory assembly 104 is engaged with the vessel closure 102 in order to allow for engagement with the top wall 108 in the manner described above and to provide a seal at the housing 124.

The housing 124 may be configured to support the one or more gas permeable membranes 126A, 126B. In this regard, the housing 124 may include an outer frame 136 and the gas permeable membranes 126A, 126B may be received and supported therein. For example, the outer frame 136 may surround and engage the edges of the gas permeable membranes 126A, 126B. In this regard, the edges of the gas permeable membranes 126A, 126B may be sealed to the outer frame 136 via any of various mechanisms such as, without limitation, insert molding, adhesives, welding, interference or other mechanical fit, etc. Thereby, all fluid communication through the respiratory assembly 104 may occur through the gas permeable membranes 126A, 126B.

Figure 6:
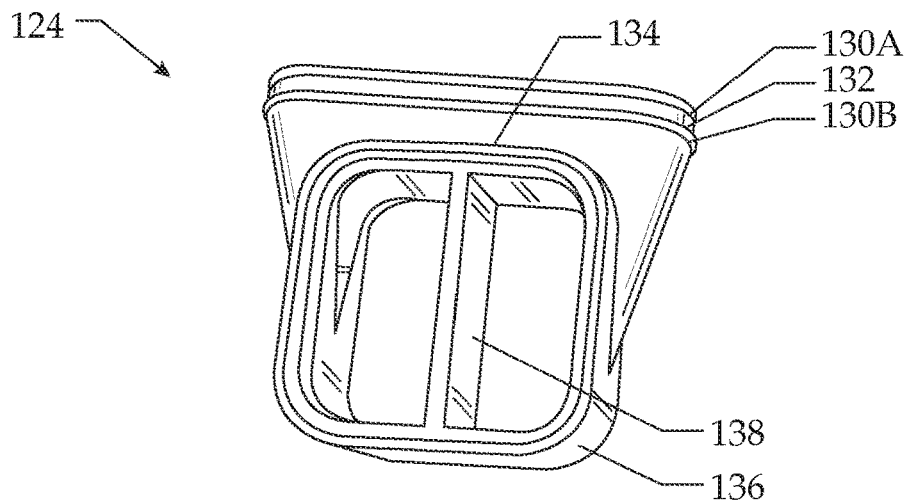
FIG. 6 is a perspective view of a housing of the respiratory assembly of FIG. 1.

Further, the housing 124 may include a support member 138. As illustrated in FIG. 6, the support member 138 may extend laterally across the housing 124 to opposing portions of the outer frame 136. Further, the support member 138 may extend vertically down to a bottom of the outer frame 136. Thereby, the support member 138 may provide additional support and bracing for the respiratory assembly 104 to resist deformation thereof during respiration through the respiratory assembly 104 and during assembly of the device.

In the illustrated embodiment, the respiratory assembly 104 includes a plurality of the gas permeable membranes 126A, 126B. Usage of multiple gas permeable membranes allows for a greater surface area for gas transfer. In this regard, the vessel closure assembly 100 may be configured such that the surface area of the gas permeable membranes is not limited to the surface area defined by the top wall 108 of the vessel closure 102. This may be accomplished by positioning the gas permeable membranes at locations and orientations that differ from those of the top wall 108 of the vessel closure 102.

In this regard, in the illustrated embodiment the respiratory assembly 104 includes two gas permeable membranes 126A, 126B. However, as may be understood, various other numbers of gas permeable membranes may be employed in other embodiments. As illustrated in FIG. 5, the gas permeable membranes 126A, 126b may extend substantially perpendicular to the top wall 108 of the vessel closure 102 and substantially parallel to one another. For example, the gas permeable membranes 126A, 126B may extend substantially perpendicular to the upper surface 108B or the lower surface 108A of the top wall 108 of the vessel closure 102. In another example, the gas permeable membranes 126A, 126B may extend at an angle relative to the upper surface 108B or the lower surface 108A of the top wall 108 of the vessel closure 102. Thereby, by positioning the gas permeable membranes 126A, 126B such that they are not coplanar or otherwise parallel with the top wall 108 of the vessel closure 102, the surface area of the gas permeable membranes through which respiration occurs may not be restricted to the surface area defined by the top wall of the vessel closure.

Accordingly, the gas permeable membranes 126A, 126B may define a relatively large total surface area through which respiration may occur. For example, in one embodiment the one or more gas permeable membranes 126A, 126B have a surface area equal to or greater than approximately 154 mm$^2$. Further, the gas permeable membranes 126A, 126B of the vessel closure 102 may have a combined flux greater than approximately 250 cc$^3$/min at 0.5 psig. By defining such a flux and/or such a surface area, the gas permeable membranes 126A, 126B may provide more than sufficient respiration for a standard sized vessel 300.

The gas permeable membranes may be constructed from various media, including without limitation, polyether sulfone, polyvinylidine fluoride, polycarbonate, polytetrafluoroethylene, polyethylene, polypropylene, cellulose acetate, polyamide, polyimide, polyetheretherketone, and composites of multiple polymers. Membranes are typically fabricated with microporous structures having average pore sizes of less than 0.6 microns to prevent bacterial passage. Larger pore sizes with greater respiration rates can be used depending upon the application.

Figure 8:
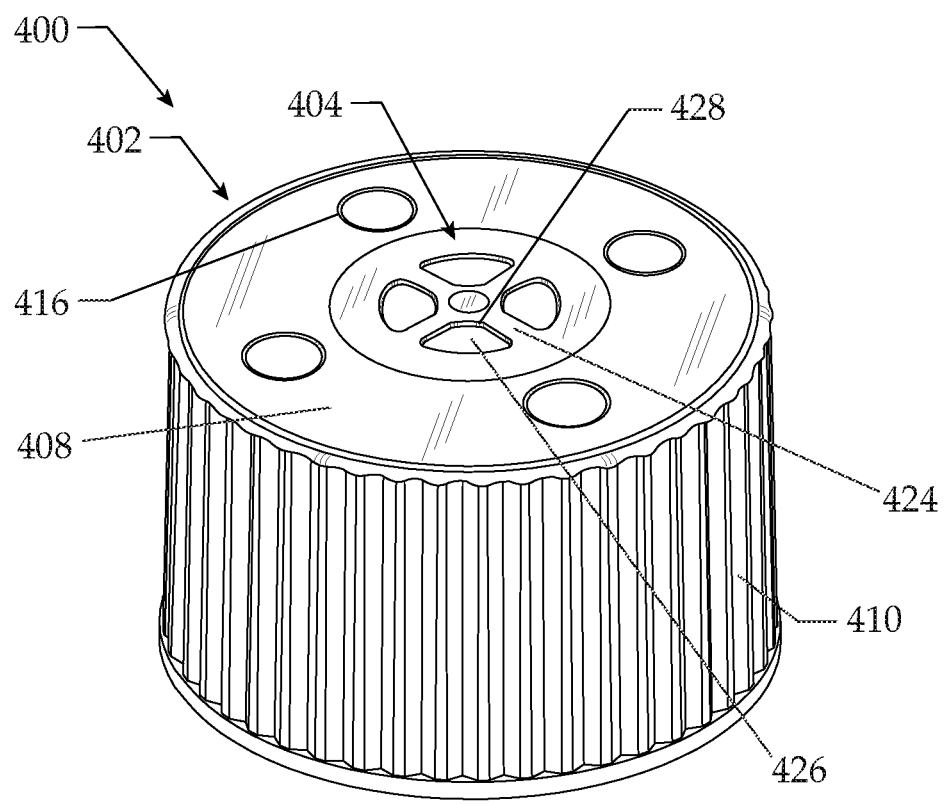
FIG. 8 illustrates a top view of vessel closure assembly according to an alternate example embodiment of the present disclosure and wherein the inserts are not shown.

Although one example configuration of the vessel closure assembly is described above, various other configurations may be employed in other embodiments. In this regard, by way of example, FIG. 8 illustrates an alternate embodiment of a vessel closure assembly 400 wherein the inserts are not shown. The vessel closure assembly 400 may be included in an assembly for processing when coupled to a suitable vessel. The assembly for processing may be aseptic as described elsewhere herein.

As illustrated, the vessel closure assembly 400 may include a vessel closure 402 configured to sealing engage the opening of a vessel such as the above-described vessel 300 of FIGS. 3-5 and 7. The vessel closure 402 may include one or more apertures 416 extending therethrough. For example, the vessel closure 402 may include a top wall 408 and a sidewall 410, and the apertures 416 may extend through the top wall. The apertures 416 may be configured to respectively receive an insert, such as the insert 106 of FIG. 1 described above, such that the insert extends therethrough.

Further, the respiratory closure assembly 400 may include a respiratory assembly 404. In the embodiment of the respiratory closure assembly 100 described above (see, e.g., FIG. 5), the respiratory assembly 104 included gas permeable membranes 126A, 126B positioned nonparallel to a plane defined by the top wall 108 of the vessel closure 102 in order to allow the gas permeable membranes to define a relatively large surface area, which may exceed a surface area of the top wall 108, if desired.

However, in other instances it may be possible to position the one or more gas permeable membranes in alternate manners and configurations. In this regard, in the vessel closure assembly 400 of FIG. 8, the respiratory assembly 404 includes a gas permeable membrane 426 positioned in contact with, and substantially parallel to, the top wall 408 of the vessel closure 402. Further, the respiratory assembly 404 includes a housing 424.

The housing 424 may be positioned at an aperture 428 defined through the top wall 408 of the vessel closure 402. In the illustrated embodiment the housing 424 is integral with the vessel closure 102. However, in other embodiments the housing 424 may comprise a separate component. Regardless, the gas permeable membrane 426 may be engaged with the housing 424. For example, as illustrated, in one embodiment the gas permeable membrane 426 may be positioned at an interior of the vessel closure 402 and engaged with a lower surface of the housing 424. This embodiment of the vessel closure assembly 400 may be restricted in terms of the surface area defined by the gas permeable membrane 426 to the surface area of the top wall 408 of the vessel closure 402. This surface area may be further restricted due to inclusion of the apertures 416 in the top wall 408 through which the inserts extend. However, the respiratory assembly 404 may define a relatively low profile (i.e., a small thickness), such that the respiratory assembly substantially avoids extending into and through the opening of a vessel when coupled thereto, so as to provide an alternative configuration.

The vessel closure assemblies disclosed herein may be assembled and then the entire devices or components thereof may be rendered substantially aseptic by, for example, gamma radiation. Alternatively, the entire devices or components thereof may be rendered substantially aseptic by exposure to steam above 121° C. for a period of time long enough to eliminate microorganisms. The entire devices or components thereof may also be rendered aseptic by chemical treatment, such as with ethylene oxide (ETO). Once rendered substantially aseptic, the vessel closure assemblies may be appropriately packaged and stored to maintain the substantially aseptic state until ready for use.

The vessel, the vessel closure assembly, and any sampling vessels or additional fluid transfer conduits, fittings, manifolds, or the like may be rendered substantially aseptic by the methods described above or others known in the art. Once rendered aseptic, the entire device may be aseptically packaged and distributed for use. The end user may open and utilize a completely closed and substantially aseptic system without risk of leaks due to the barbed or luer connectors extending from a vessel.

However, in an additional embodiment at least of one of the one or more inserts may comprise a barbed fitting. By way of example, the barbed fitting may be configured to face the exterior of the vessel. By way of further example, the barbed fitting may be configured to face inward from the cap toward the interior of the vessel. By way of yet another example, the insert may consist of two barbed fittings, one facing the exterior of the vessel and one facing the interior of the vessel. Thereby, fluid conduits such as the tubing described elsewhere herein may be engaged to the barbed fittings to extend into the interior of the vessel, extend outside of the vessel, or both extend into the interior and exterior of the vessel.

In another embodiment a method of growing cells in suspension in a vessel is provided. The method may include adding media to the vessel. Further, the method may include adding cells to the vessel. The method may additionally include providing conditions appropriate for growth of the type of cells to be grown.

The vessel employed in the method may have an opening. The vessel may additionally include a vessel closure sealingly engaged to the opening of the vessel. The vessel closure may include one or more apertures extending through the vessel closure. Further, the vessel may include one or more inserts extending through the one or more apertures. A respiratory assembly may be engaged with the vessel closure. The respiratory assembly may include a housing. One or more gas permeable membranes may be engaged with the housing. In this regard, in some embodiments the method may employ one of the embodiments of vessel closure assemblies 100, 400 described above.

The foregoing descriptions of vessel closure assemblies, methods of manufacturing vessel closure assemblies, and methods of utilizing vessel closure assemblies illustrate and describe various embodiments. As various changes can be made in the above embodiments without departing from the scope of the present disclosure recited and claimed herein, it is intended that all matter contained in the above description or shown in the accompanying figures shall be interpreted as illustrative and not limiting. Furthermore, the scope of the present disclosure covers various modifications, combinations, alterations, etc., of the above-described embodiments that all are within the scope of the claims. Additionally, the disclosure shows and describes only selected embodiments of the present disclosure, but the present disclosure is capable of use in various other combinations, modifications, and environments and is capable of changes or modifications within the scope of the disclosure as expressed herein, commensurate with the above teachings, and/or within the skill or knowledge of artisans in the relevant art. Furthermore, certain features and characteristics of each embodiment may be selectively interchanged and applied to other illustrated and non-illustrated embodiments of the present disclosure without departing from the scope of the present disclosure.

The invention claimed is:

1. An assembly for processing fluids comprising:
   a vessel having an opening;
   a vessel closure sealingly engaged to the opening of the vessel, the vessel closure comprising a top wall and a sidewall, the sidewall connected to and extending perpendicular to the top wall, the top wall including one or more apertures extending therethrough;
   one or more inserts extending through the one or more apertures; and
   a respiratory assembly configured to allow respiration of the vessel to an environment outside of the vessel, the respiratory assembly comprising:
      a housing seperably engaged with the top wall of the vessel closure to secure the housing to the vessel closure; and
      one or more gas permeable membranes engaged with the housing, the one or more gas permeable membranes positioned flush with or below the top wall when the housing is secured to the vessel closure.

2. The assembly of claim 1, wherein the vessel closure has a combined flux greater than approximately 250 cc$^3$/min at 0.5 psig.

3. The assembly of claim 1, wherein the one or more inserts comprise a fluid conduit.

4. The assembly of claim 3, wherein one end of the fluid conduit terminates at a first terminus approximately inside the vessel closure.

5. The assembly of claim 3, wherein the vessel closure has a surface facing an interior surface of the vessel when the vessel closure sealingly engages the vessel, and one end of the fluid conduit terminates at a first terminus approximately flush with the vessel closure surface facing the interior surface of the vessel.

6. The assembly of claim 3, wherein one end of the fluid conduit terminates at a first terminus inside the vessel and the other end of the fluid conduit terminates at a second terminus outside the vessel closure and outside the vessel.

7. The assembly of claim 3, wherein one end of the fluid conduit terminates at a second terminus outside the vessel and at least partially outside the vessel closure.

8. The assemble of claim 7, wherein the second terminus outside the vessel and at least partially outside the vessel closure further comprises a fitting selected from the group consisting of an aseptic connector, an air-tight fitting, a plug, and a needleless luer access site.

9. The assembly of claim 1, wherein the one or more inserts comprise one or more anchors, wherein a fluid conduit passes through each anchor the fluid conduits terminating at a first terminus inside the vessel and terminating at a second terminus outside the vessel, the fluid conduit terminus located outside the vessel further comprising an aseptic connector.

10. The assembly of claim 1, wherein the one or more gas permeable membranes have a surface area equal to or greater than approximately 154 mm$^2$.

11. The assembly of claim 1, wherein at least of one of the one or more inserts comprise a barbed fitting comprising two attachment points whereby tubing may be engaged to the barbed fitting at a first attachment point and extend into the interior of the vessel and tubing may be engaged to a second attachment point and extend outside of the vessel.

12. The assembly of claim 1, wherein the respiratory assembly engages the vessel closure via interference fit.

13. The assembly of claim 1, comprising a plurality of gas permeable membranes.

14. The assembly of claim 13, wherein the plurality of gas permeable membranes extend substantially parallel to one another.

15. The assembly of claim 14, wherein the plurality of gas permeable membranes extend substantially perpendicular to the top wall of the vessel closure.

16. The assembly of claim 1, wherein the vessel comprises an Erlenmeyer flask.

17. An assembly for processing fluids comprising:
a vessel having an opening;
a vessel closure sealingly engaged to the opening of the vessel, the vessel closure comprising a top wall and a sidewall, the sidewall connected to and extending perpendicular to the top wall, the top wall including one or more apertures extending therethrough;
one or more inserts extending through the one or more apertures; and
a respiratory assembly configured to allow respiration of the vessel to an environment outside of the vessel, the respiratory assembly comprising:
a housing seperably engaged with the top wall of the vessel closure to secure the housing to the vessel closure; and
one or more gas permeable membranes engaged with the housing that extend substantially perpendicular to the top wall of the vessel closure.

18. A substantially aseptic assembly for processing fluids, the assembly comprising:
a vessel having an opening;
a vessel closure sealingly attached to the opening of the vessel, the vessel closure comprising a top wall and a sidewall, the sidewall connected to and extending perpendicular to the top wall, the top wall defining one or more apertures extending therethrough;
one or more inserts extending through the one or more apertures; and
a respiratory assembly configured to allow respiration of the vessel to an environment outside of the vessel, the respiratory assembly comprising:
a housing separably engaged with the top wall of the vessel closure to secure the housing to the vessel closure; and
one or more gas permeable membranes engaged with the housing; and
wherein the one or more gas permeable membranes extend substantially perpendicular to the top wall of the vessel closure.

19. The assembly of claim 18, wherein one or more of the inserts comprise a fluid conduit.

* * * * *